United States Patent [19]

Krieg

[11] Patent Number: 4,688,037
[45] Date of Patent: Aug. 18, 1987

[54] ELECTROMAGNETIC COMMUNICATIONS AND SWITCHING SYSTEM

[75] Inventor: James C. Krieg, East Peacham, Vt.

[73] Assignee: McDonnell Douglas Corporation, Long Beach, Calif.

[21] Appl. No.: 369,815

[22] Filed: Apr. 19, 1982

Related U.S. Application Data

[63] Continuation of Ser. No. 179,421, Aug. 18, 1980, abandoned.

[51] Int. Cl.[4] .................. G08C 19/00; G09B 21/00
[52] U.S. Cl. .................. 340/825.72; 340/573; 340/365 R; 340/686; 324/207; 324/247; 324/226; 324/260; 434/43; 434/112; 250/491.1; 342/448; 342/449
[58] Field of Search .............. 340/825.72, 573, 365 R, 340/365 S, 365 P, 365 A, 686; 343/112 R, 119, 100 AD, 448–450; 324/207, 208, 244, 247, 226, 260; 318/16; 455/73, 80, 82; 250/491, 491.1; 434/112, 114, 43

[56] References Cited

U.S. PATENT DOCUMENTS

| | | | |
|---|---|---|---|
| 3,379,885 | 4/1968 | Nork | 250/338 |
| 3,651,512 | 3/1972 | Summers | 340/286 |
| 3,668,565 | 2/1972 | Kuipers | 324/34 |
| 3,678,283 | 7/1972 | La Baw | 250/216 |
| 3,818,448 | 6/1974 | Wilkins | 340/825.19 |
| 3,848,249 | 11/1974 | Meiri | 340/365 S |
| 3,854,131 | 12/1974 | Vanderheiden et al. | 340/365 L |
| 3,925,779 | 12/1975 | Gerstenhaber | 340/365 R |
| 3,983,474 | 9/1976 | Kuipers | 324/43 |
| 3,986,030 | 10/1976 | Tettscher | 340/365 P |
| 4,017,858 | 4/1977 | Kuipers | 343/100 |
| 4,048,439 | 9/1977 | Gabus | 340/365 R |
| 4,054,881 | 10/1971 | Raab | 343/112 |
| 4,081,623 | 3/1978 | Vogelex | 179/90 BD |
| 4,091,273 | 5/1978 | Fuller et al. | 455/603 |
| 4,197,855 | 4/1980 | Lewin | 128/653 |

OTHER PUBLICATIONS

"Smart Machines Learn to See, Talk, Listen, Even Think for Us"; Smithsonian, 1980; Richard M. Restak, pp. 48–57.

Primary Examiner—Donnie L. Crosland
Attorney, Agent, or Firm—Price, Heneveld, Huizenga & Cooper

[57] ABSTRACT

An electromagnetic communications and switching system provides for line-of-sight remote selection and actuation of a wide variety of apparatus. The system has a plurality of radiating antennas having independent components defining a reference coordinate frame. A transmitter is provided for applying electrical signals to the antennas which generate a plurality of radio frequency electromagnetic fields. The signals are multiplexed so that the electromagnetic fields are distinguishable from one another. An array of control positions is provided that is fixed with respect to the reference coordinate frame. A plurality of receiving antennas are provided which are adapted for mounting on the head of an operator. The receiving antennas are provided with independent components for detecting and measuring the components of the electromagnetic fields. A sight couples the eyes of the operator and the array of control positions. The sight is mounted on the head of the operator and defines a line-of-sight for the operator. A processor is provided for converting the components of the electromagnetic fields received by the receiving antennas into the position and orientation of the receiving antennas with respect to the radiating antennas. Using the sight, the operator selectively points to a desired control position and the processor determines which control position is being chosen by determining the position and orientation of the operator's head and thus the line-of-sight of the operator.

3 Claims, 6 Drawing Figures

ELECTROMAGNETIC COMMUNICATIONS AND SWITCHING SYSTEM

This is a continuation of application Ser. No. 179,421, filed Aug. 18, 1980 now abandoned.

BACKGROUND OF THE INVENTION

The invention relates generally to electro-optical communications and switching systems and more particularly to an electro-optical switching system employing a radio frequency electromagntic coupling.

It can be appreciated that there are many functions which particular persons or persons particularly situated cannot readily and conveniently accomplish by the use of hands, or other bodily movements, or by voice control. These individuals include persons who are physically handicapped to the extent of not having the use of their hands, limbs, or voice and those that while having all of their normal faculties are so engaged or otherwise constrained so as to be unable to effectively perform or control certain desired tasks. The latter category would include persons having both hands and perhaps both feet engaged in controlling machinery which requires additional control information from the operator.

In the field of handicap communications systems, a variety of additional body outputs have been used to control a communications systems. For example, prior art handicap communications systems are found that utilize such body outputs as breathing, tongue pressure or movement of the hand, leg, head, eye or some other controllable portion of the body for actuating the system. In many of these prior art communications devices the user is required to learn a new language and implementing the language or code of the device is often fatiguing. In one prior art electro-optical handicap communications system the eye motion of an operator is used to operate a keyboard-like accessory. The keyboard accesory includes a plurality of infrared responsive sensors disposed in a keyboard-like array. An infrared source is then directed into the eyes of the user who selectively actuates elements on the keyboard by dwelling his eyes upon an infrared responsive sensor on the keyboard. Infrared energy reflected from the operator's eye to the keyboard actuates the infrared responsive sensor to which the operator directs his eyes. By selectively dwelling his eyes upon various elements on the keyboard, the operator may assemble a message. While a great number of users may use this device regardless of the extent of their disability and without the need of learning a machine language, the system is prone to interference from environmental sources of light and can become completely inoperable under certain lighting conditions. Other electro-optical keyboard communications devices have employed infrared and other light energy sources mounted directly on the head of the user. In this case, the user directs the source of light energy to a desired photosensitive element with head movement. However, these devices are also subject to light interference problems and all of these systems require provision of an active photosensitive keyboard which is expensive.

The development of larger and faster aircraft both commercial and military has resulted in an increase in the number of sophisticated and complex airborne avionics systems which have substantially increased the amount of cockpit instrumentation and the workload of the crew of the aircraft. Furthermore, often these new avionic systems, which include navigational aids, engine performance monitoring systems and automatic flight control systems, require some type of constant actuation during flight. The proliferation of such avionic equipment is most evident in modern military aircraft where in addition to such systems as navigation and engine control, sophisticated radar systems and weapon delivery systems are provided. While commercial and military pilots are trained to manually operate these systems, often critical flight regimes are encountered when the activities required in manually switching the various cockpit instrumentation may cause a measurable reduction in the operational effectiveness and subsequently in the flight safety margin maintained by the pilot. Although the problem may be more severe in a military aircraft involving a single pilot where critical airborne operations include air-to-air refueling, low level flight, aircraft carrier landing and takeoff, ordinance delivery patterns and air combat maneuvering, the commercial pilot is similarly burdened with the work load and concentration involved in landing and taking off from congested commercial airports. The prior art has attempted to alleviate this problem with electro-optical switching systems including a plurality of photosensitive visually actuated switches. Each of the switches is used to control one of a plurality of avionic systems. The switches are infrared sensitive and the pilot is provided with a helmet including means for generating a collimated beam of infrared energy which the pilot directs to the photosensitve switches with a helmet mounted reticle. However, these systems do at times encounter environmental light source interference problem and involve the cost and complexity of installing control switches which are both photosensitive and manually actuable.

The art of tracking remote objects with electromagnetic radiation is highly developed. Prior art remote object position and orientation locators have employed a plurality of independent radiating antennas defining a source of electromagnetic radiation; a plurality of independent receiving antennas having a known relationship with respect to a remote object and means associated with the receiver for measuring the components of the received electromagnetic fields for calculating remote object position and orientation. Such systems may be used for example for guiding an aircraft to a landing site, guiding an excavating device, or tracking targets and aiming ordinance. In the latter case, the source of electromagnetic radiation is fixed with respect to the frame of the aircraft and the receiver is mounted on the pilot's helmet in a calibrated relationship with respect to a helmet mounted reticle. The analyzing means associated with the receiver repetitively calculates the position and orientation of the pilot's head with respect to the air frame and the pilot visually designates and/or tracks the target with the helmet mounted reticle to initially aim the ordinance. Purely optical systems for carrying out the same functions are also found in the environment of an aircraft cockpit employing a plurality of cockpit mounted infrared sources and a plurality of helmet mounted photodectors. Analyzing means connected to the pilot's helmet mounted photodetectors uniquely establish the position and orientation of the pilot's helmet. However, the optical versions of these systems are sensitive to light interference and function accurately within a very limited range of operator movement. Neither the light or radio frequency electromagnetic energy coupled systems as they exist are capable of functioning as an electro-optical communications and remote switching device.

SUMMARY OF THE INVENTION

These and other problems in the prior art are solved by provision of a radio frequency electromagnetic energy coupled communications and switching system for line-of-sight selection and remote actuation of a wide variety of apparatus. This system comprises a plurality of radiating means having independent components defining a reference coordinate frame. Means are provided for applying to the plurality of radiating means electrical signals which generate a plurality of radio frequency electromagnetic fields. Each electromagnetic field is associated with an individual radiating means. The electromagnetic fields thereby created are distinguishable from one another. An array of control positions are defined with respect to the reference coordinate frame by calibration or measurement. In the case of a handicap communications system, the array of control positions may comprise an alpha-numeric typewriter-like keyboard. In the case of a switching system for use by an equipment operator, the array of control positions may be defined by a plurality of switches which are normally manually actuated or the control positions may simply be defined by the various apparatus which the equipment operator wishes to actuate. A plurality of receiving means or antennas are provided, the receiving antennas being adapted for mounting on the head of an operator. The receiving means are provided with a plurality of independent components for detecting the components of the electromagnetic fields transmitted by the plurality of radiating means. Sighting means for defining the line-of-sight for an operator is provided comprising a reticle, or the like, adapted for mounting on the head of an operator. Using the reticle provided, the operator selectively actuates any one of a number of control positions by sequentially aiming the reticle at predetermined control positions. Analyzing means associated with the receiving means is provided for converting the received components of the electromagnetic fields into receiver position and orientation with resepct to the radiating means. Since the reticle establishes a relationship between the line-of-sight of the operator and the receiving means, the analyzing means can determine which control positions the operator points the reticle at. The operator may actuate selective pieces of equipment by pointing to particular control positions, or the operator may assemble a message by sequentially dwelling the reticle on control positions associated with particular alpha-numeric characters. In the case of a communications system the array of control positions is associated with an alpha-numeric keyboard and the analyzing means is connected to a printer so that the operator can assemble a hard copy of the messages created by sequentially dwelling the reticle on individual characters of an alpha-numeric keyboard. This communications system allows the user to communicate with conventional language skills and thus eliminates the effort of implementing fatiguing codes. The system is virtually free from interference and the system enhances the speed at which the user can communicate since the analyzing means may also be provided with a plurality of memories for storing frequently used preassembled messages or phrases.

DESCRIPTION OF THE PREFERRED EMBODIMENTS

Figure 1:
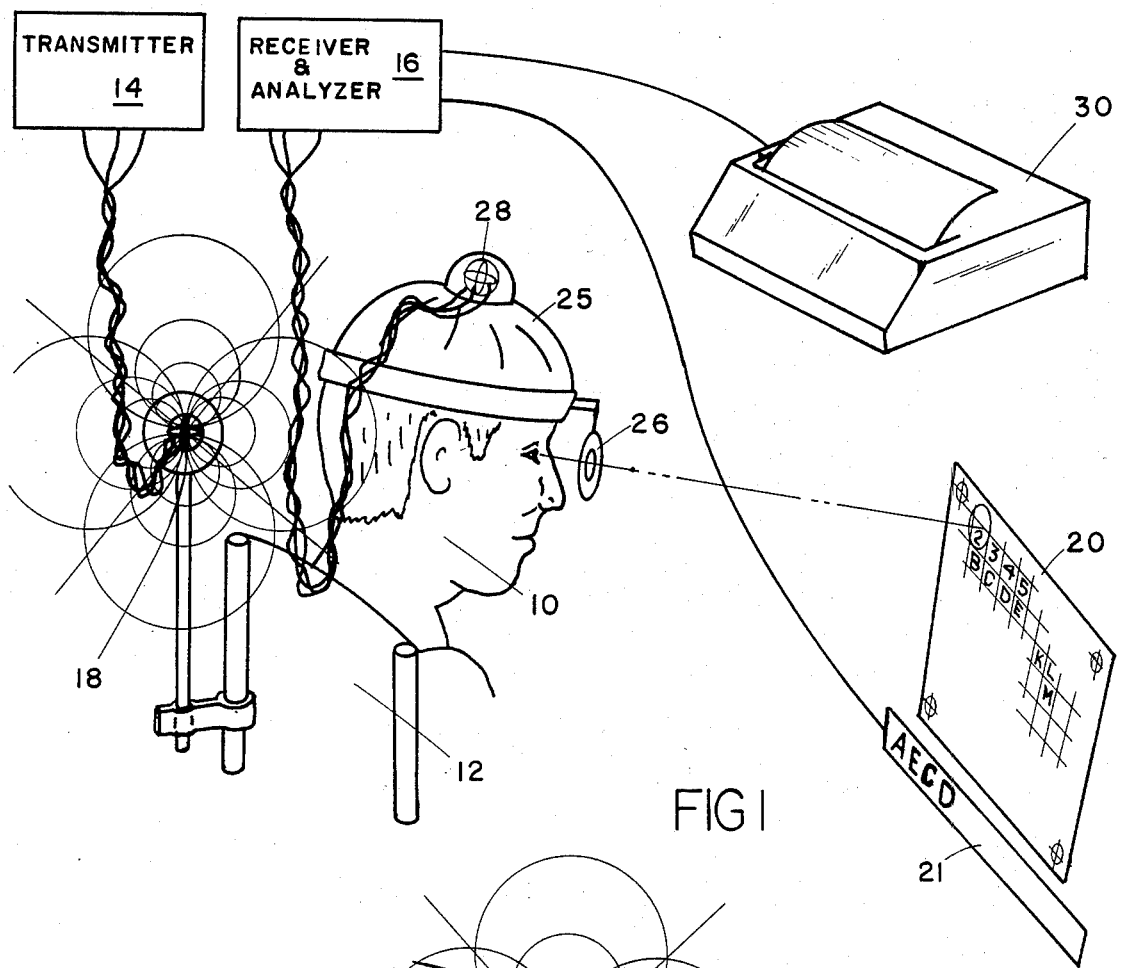
FIG. 1 is a perspective view of an electromagnetic handicap communications system and switching system constructed according to the present invention.
Figure 2:
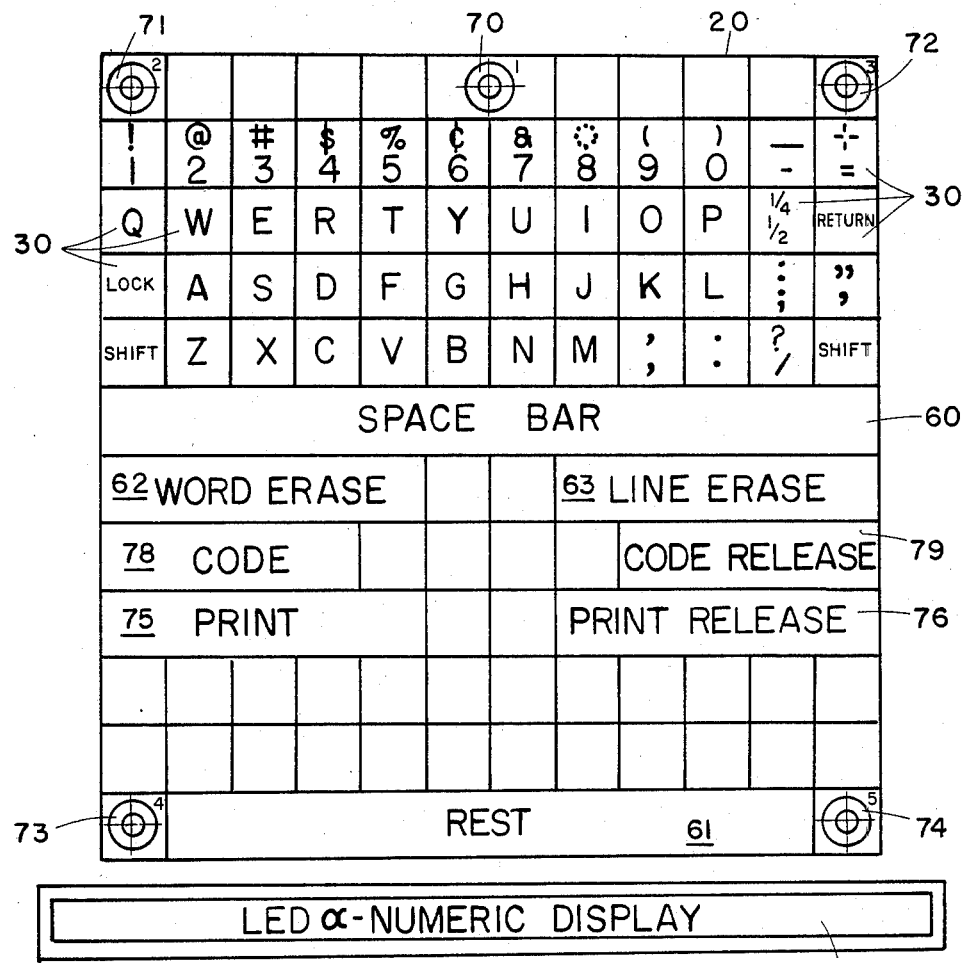
FIG. 2 is an elevational view of a keyboard and digital display employed in the embodiment of the invention illustrated in FIG. 1.

With reference now to FIG. 1, a handicap communications system embodying the electromagnetic communication and switching system of the present invention is illustrated. In this case, the user or operator 10 of the system may be a quadraplegic seated in a wheelchair 12. The operator 10 need only have sufficient head movement to provide approximately a 60° field of regard to operate the communications device. The system includes a transmitter 14 which may operate in an open loop or closed loop fashion with respect to a receiver and analyzing means 16. The transmitter 14 includes a plurality of radiating antennas 18 having independent components defining a reference coordinate frame. The receiver includes a plurality of receiving antennas 28 having a plurality of independent components. Since the separation distance between the transmitting and receiving antennas 18 and 28 is relatively small a near field or magnetic field coupling between the antennas is achieved and each of the independent components of both the transmitting and receiving antennas is a loop antenna providing a dipole or toroidal shaped near field electromagnetic field. At least two and preferably three mutually orthogonal transmitting loop antennas are centered at 18. The transmitting antennas 18 may be disposed at any convenient location which will minimize field distortion caused by nearby structures and, for example, they may be mounted on the back of the wheelchair 12 for positioning directly adjacent the operator's head. The transmitter 14 includes means for applying to each of the three orthogonally oriented loop antennas 18 an electrical signal which generates a plurality of radio frequency electromagnetic fields, each electromagnetic field being distinguishable and associated with a particular orthogonal loop antenna. As best illustrated in FIG. 2, the keyboard accessory 20 comprises a typewriter keyboard-like alpha-numeric array of characters. Preferably, an alpha-numeric display is disposed directly below the keyboard at 21 for providing a current indication of the nature of the message being assembled by the operator.

The operator 10 wears a lightweight. baseball-type of cap, sun visor type harness or eyeglass type of device at 25. The cap 25 includes sighting means for defining the line-of-sight of the operator comprising a small plastic ring reticle or pointing device 26 mounted in front of the operator's eyes on the cap 25. The cap 25 also includes the receiving antennas 28 which are thus adapted for mounting on the head of the operator 10 along with the cap 25. The plurality of receiving antennas 28 comprise at least two and preferably three mutually orthogonal loop antennas. Each of the three mutually orthogonal loop antennas detects components of the three electromagnetic fields emanating from the plurality of radiating means 18. Preferably, three mutually orthogonal loop antennas are provided at both 18 and 28. However, if certain boundry assumptions can be made with regard to the orientation and position of the receiving antennas 28 with respect to the radiating antennas 18, one of either the radiating antennas 18 or receiving antennas 28 may be eliminated. That is to say, two mutually orthogonal radiating antennas 18 may transmit to three mutually orthogonal receiving antennas 28.

The sighting means for defining the line-of-sight of the operator, which in this case comprises a reticle 26 fixed on the cap 25, may also include a light source or light pointer, not illustrated herein for indicating to the patient when the reticle 26 is accurately aligned with a predetermined alpha-numeric character on the keyboard 20. The operator 10 operates the device by selectively pointing the reticle 26 to predetermined control positions associated with individual alpha-numeric characters disposed on the keyboard 20. Analyzing means is associated with the receiver at 16 for converting the components of the electromagnetic fields received by each of the mutually orthogonal loop antennas 28 into remote object position and orientation with respect to the radiating means 18. That is to say, the analyzing means 16 determines the position and orientation of the receiving means 28 with respect to the transmitting means 18. since the receiving means 28 are provided with a fixed relationship with regard to the head of the user 10 and the reticle 26, the position and orientation of the receiving means 28 is an accurate representation of the line-of-sight of the user through the reticle 26 and thus is representative of the control position to which the operator is pointing the reticle 26.

The operational theory of remote object position and orientation locators and suitable components for the transmitter 14, the radiating means 18, the receiver and the analyzer 16 are known in the prior art and are shown in prior U.S. Pat. No. 4,054,881 to Raab entitled REMOTE OBJECT POSITION LOCATOR and U.S. Pat. No. 3,983,474 to Kuipers entitled TRACKING AND DETERMINING ORIENTATION OF OBJECTS USING COORDINATE TRANSFORMATION MEANS SYSTEM AND PROCESS. Operating theory suitable apparatus are also disclosed in pending U.S. Pat. No. 4,298,874 entitled METHOD AND APPARATUS FOR TRACKING OBJECTS to Kuipers et al, and U.S. Pat. No. 4,314,251 entitled REMOTE OBJECT POSITION LOCATOR to Raab. The apparatus and theory of operating of the transmitter 14, the radiating means 18, the receiver and analyzer 16 are adequately disclosed in all of the aforementioned commonly assigned patents and patent applications and the disclosures of these patents and patent applications are hereby incorporated by reference. The Kuipers patent and patent application disclose remote object position and orientation locators which, in preferred embodiments, employ radiating means 18 which generate a plurality of electromagnetic fields that effectively nutate about a pointing axis extending between the radiator 18 and the object being tracked containing the receiving means 28. In preferred embodiments, the systems disclosed in the Kuipers patents and patent applications are adapted for closed loop operation. That is to say, the transmitter and receiver exchange information usually comprising the pointing angles of both the radiator and the receiver. The patent and patent application to Raab disclose remote object position and orientation locators adapted for open loop operation in the near field. That is to say, like the system illustrated in FIG. 1 of the present application, the transmitter and radiator are independent of the receiver and analyzer.

Figure 3:
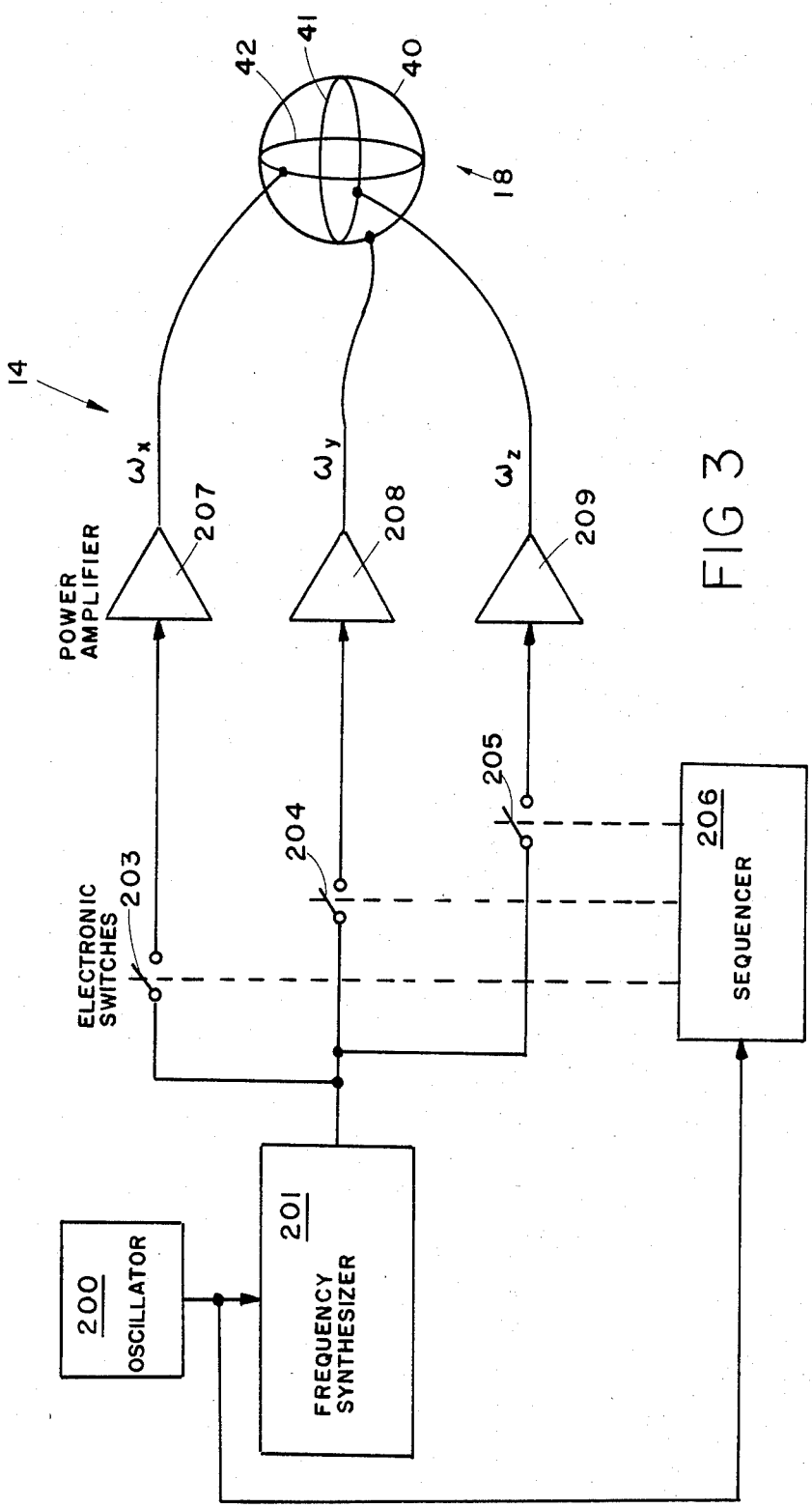
FIG. 3 is a schematic representation of a time division multiplexed transmitter suitable for use with the present invention.

Although the signals applied to the plurality of radiating means 18, may be multiplexed in any one of a number of fashions, FIG. 3 depicts a block diagram of a transmitter 14 which applies time division multiplexed signals to each of the three mutually orthogonal loop antennas 40, 41 and 42. All signals in the transmitter 14 are derived from a stable oscillator 200 by a frequency synthesizer 201. The derived radio frequency signals are switched to the power amplifiers 207, 208 and 209 by gates 203, 204 and 205 which operate under the control of a sequencer 206. The power amplifiers 207, 208 and 209 produce excitation voltages $\omega_x$, $\omega_y$, and $\omega_z$ as inputs to the antennas 42, 40 and 41, respectively. The mutually orthogonal loop antennas 40 through 42 produce a near field magnetic dipole field pattern.

Figure 4:
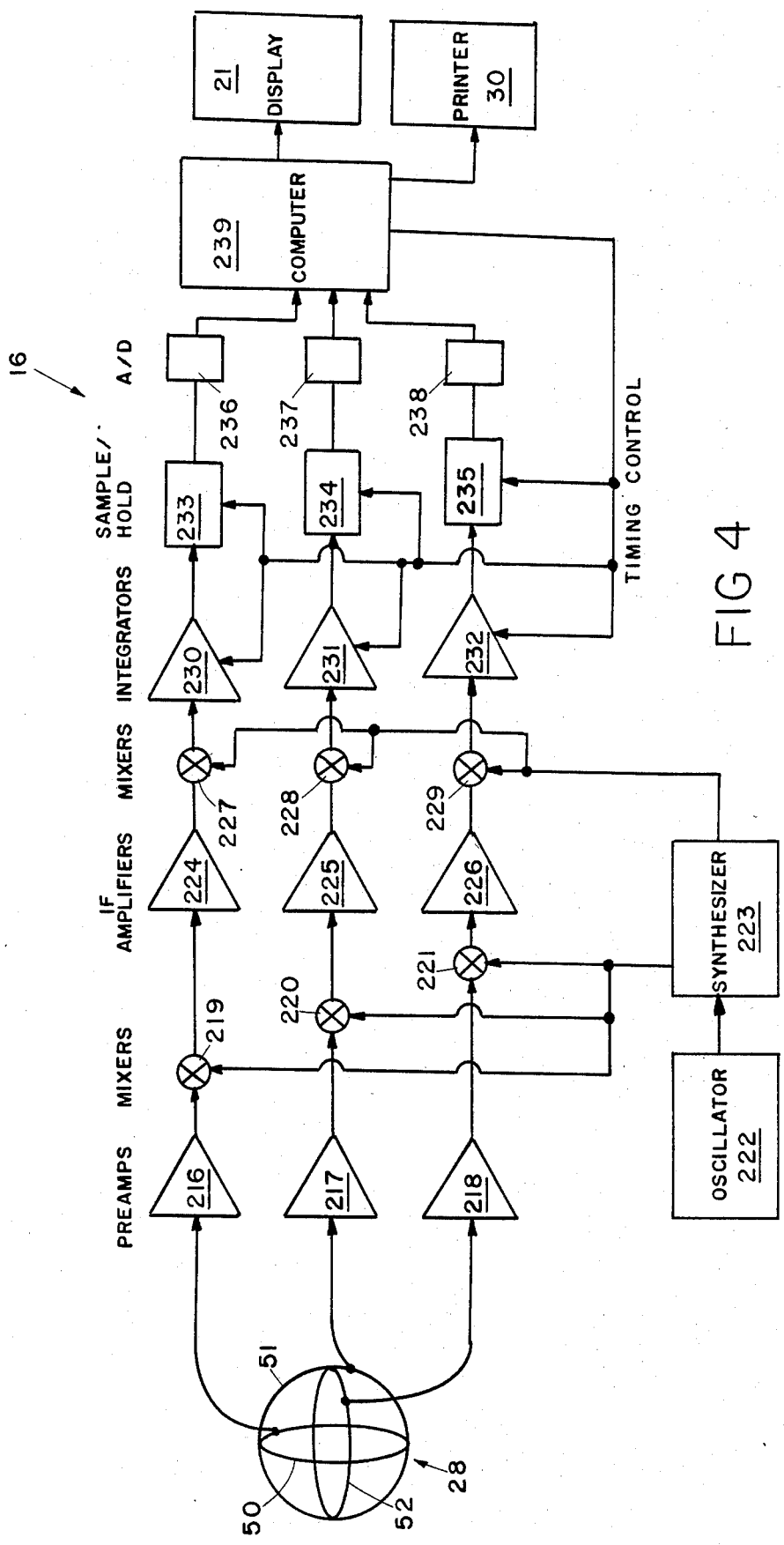
FIG. 4 is a schematic representation of a time division multiplexed receiver suitable for use with the present invention.

A receiver and analyzing means suitable for use in a time division multiplexed system is illustrated in FIG. 4. Signals are received by loop antennas 50, 51 and 52 and preamplified by preamplifiers 216, 217 and 218. After preamplification the three received signals are converted to an intermediate frequency by mixers 219, 220 and 221 which are driven by signals produced by an oscillator 222 and a synthesizer 223. For each of the receiving loop antennas 50 through 52, the receiver distinguishes a component associated with each of the three transmitting loop antennas 40 through 42. All signals and timing in the receiver are derived from one master oscillator. Not illustrated herein is apparatus for phase locking to the received signal which may be added and which is standard technology. Intermediate frequency signals are amplified by amplifiers 224, 225 and 226. The amplified intermediate frequency signals are mixed with signals of the same frequency in mixers 227, 228 and 229. The outputs of these mixers are integrated by integrators 230, 231 and 232 and sampled by 233, 234 and 235. Outputs are acquired by the computer 239 which performs the required mathematical operations on the nine components received from the three orthogonal receiving antennas 50 through 52 to extract information representative of the position and orientation of the receiving means 28 with respect to the transmitting means 18. However, in some embodiments of the invention the IF stages of the circuit may be eliminated and the mixers, oscillator and synthesizer may be replaced by a simple multiplexer with a single A/D converter.

Figure 5:
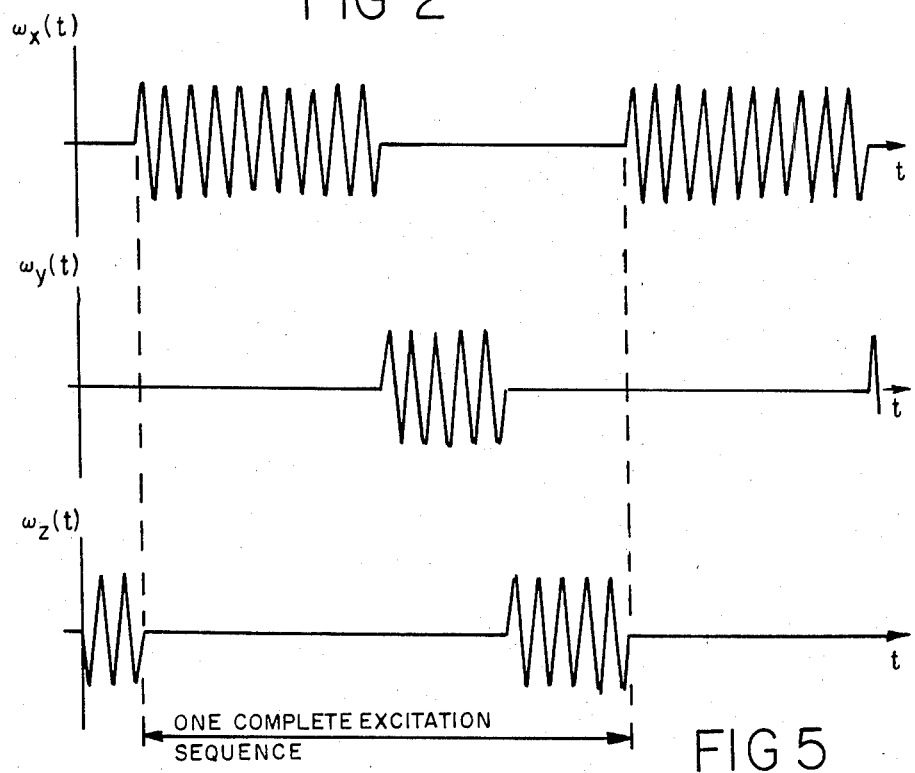
FIG. 5 is a plot of ideal voltage versus time for a suitable time division signal format.

FIG. 5 illustrates a pulsed carrier wave signal format suitable for use in a time division multiplexed system. The three axes of the transmitting antenna are excited sequentially by signals of the same frequency. The duration of the three pulses are known (fixed) with the X axis excitation pulse longer than the others to allow the receiver to establish synchronization thereby knowing which received signals to attribute to which transmitting axis. To allow rejection of multipath effects, a "dead space" may be inserted between the pulses to allow time for echoes to die out. If multipath interference was not a problem, all three axes could be excited simultaneously by signals of different frequencies or by signals modulated by different spread spectrum codes. These are engineering design decisions that must be made for each application of the disclosed conept.

Referring now again to FIG. 1, the operation of the electromagnetic communications and switching system of the present invention will be described in further detail. Preferably, the keyboard or target chart 20 and digital display 21 are mounted directly in front of the user or operator 10 for ease of viewing. The keyboard and digital display may for example be attached directly to the arms of the chair in which the operator is seated. With reference now to FIG. 2, it is illustrated that the keyboard 20 and display 21 are a modified representation of the familiar typewriter keyboard with some additional keys. The keys are denoted by each of the squares 30 and are arranged in such a manner that each alpha-numeric character represents and occupies a known position and space relative to the head mounted reticle 26 at a fixed distance from the reticle. The unfilled squares or empty keys are non-operative zones which allow the user to rest and are available for character font expansion or memory capability. In the case where the user has at least a 60° range of head movement, 5° changes in head movement will be sufficient to direct the reticle to alpha-numeric characters disposed in adjacent rows or columns. A 5° resolution with regard to the angular orientation of the patient's head is well within the system tolerance and allows sufficient user tolerance. Although, it should be understood that the choice of a 5° grid is somewhat arbitrary since any grid that is larger than the system tolerance and which a user is capable of choosing elements from is satisfactory. Areas that are blocked off completely across the chart, such as the space bar section 60 and the rest section 61 are elevation position sensitive only. Azimuth is not germane when the operator is directing the reticle into one of these areas. This is provided for ease in use and to make the keyboard functionally identical to a typewriter. Areas that are blocked off partially across the keyboard, such as the word erase, and line erase sections 62 and 63, respectively, are elevation senstive within 5° but have a wide azimuth tolerance which make them easier to use. The rest position 61 is elevation sensitive only and represents a non-operational mode for the computer within the analyzer 16 and is located at the bottom of the chart 20 to allow both rest and convenience for the user during a period when the user will probably want to view the electronic dispaly 21 in a static condition.

Five calibration reticles 70 through 74 define the field of operation for the computer. With a 5° grid system within which line-of-sight takes on character meaning, calibration is required prior to use, especially for those embodiments where the radiating means 18 is not fixed with respect to the keyboard 20 and those instances where a user's head may be naturally canted from the horizontal and vertical centerlines. The calibration procedure must be repeated in the event of user position changes because of fatigue or toilet requirements during operation.

Use of the head mounted reticle 26 effectively immobilizes the user's eye so that the line of sight measurement is a function solely of head position, not eye movement. With the system turned on, the user or patient looks at the calibration reticles on the keyboard 20 in the order in which they are numbered. This is done by having the user move his head into such a position that his or her head mounted reticle is superimposed on the calibration reticle of the chart. Absolute accuracy is not required but the 5° accuracy requirement must be met. The user holds his sight on each reticle position for a preset and selectable time and then moves to the next numbered calibration reticle. Having accomplished this operation, the system is aligned and the computer within the analyzer 16 establishes a 5° grid system relative to the calibration or field-of-regard. With this grid system established, the computer will have stored in memory each character and/or function that exists on the chart within each 5° segment relative to the line-of-sight within the field-of-regard. The user then, in order to assemble a message has only to point his head mounted reticle 26 at the letter, number or function he desires to implement and hold it there for the preset and selectable time period. This allows the user's line-of-sight or head position to be calculated, compared to the image of the grid stored in the computer and the letter, number or function is recalled from memory and displayed and/or printed. The computer time to accomplish this activity is in the order of milliseconds and is not discernable to the user. Having chosen an alpha-numeric character, the user then moves his head to line the reticle on the next predetermined character. Once the reticle is held upon the next predetermined character for the required time period, the process is again repeated for subsequent characters necessary to assemble the desired message. From this point on it can be readily visualized that this activity is similar to utilizing a typewriter in a one finger "hunt and peck" mode.

The display 21 is a simple light emitting diode (LED) or similar type electronic alpha-numeric display. In addition to the display 21, the output of the analyzer 16 may be connected to a low cost printer 30. The electronic display 21 provides a readout of a 40 character or conveniently large character section of the message being assembled. A hard copy of the message assembled may be generated by the printer 30 and the print and print release sections 75 and 76 are employed for operating the printer. In the typical mode of operation the operator assembles one portion of a message on the display 21 and when he is satisfied that it is correct he directs the printer to make a copy of the message.

A number of variations to the basic system are possible. For example, keys designated as code and code release may be provided at 78 and 79, respectively. When the code key 78 is activated a number of canned messages stored in the computer are displayed in response to activating a designated key. For instance, the user may activate the code key and then the letter N or any so designated key. The computer would then respond by displaying and/or printing the user's full name. Additionally, in this mode, activating the letter A or any so designated key would have the computer display and/or print the patient's address. To return to the normal mode of operation, the patient need only activate the code release key. The code mode of operation requires software modifications only and is extremely flexible relative to volume and content of the canned messages, assuming of course adequate computer memory. Other potential modifications of the device include a telephone interconnection or a modified keyboard that may be used to play a musical instrument.

Figure 6:
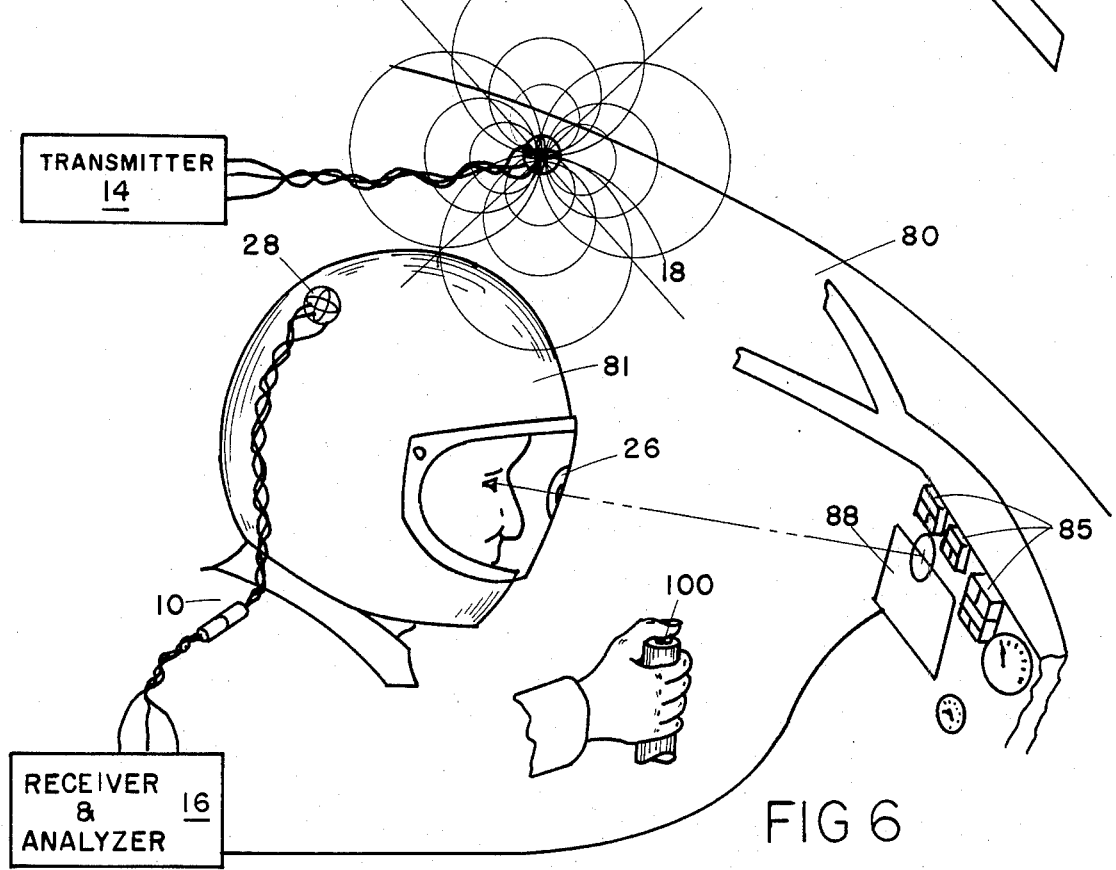
FIG. 6 is a perspective view of an embodiment of the electromagnetic communications and switching system of the present invention employed in the cockpit of an aircraft.

The electromagnetic communications and/or switching system of the present invention may have utility in applications other than that of a handicap communications system. For example referring to FIG. 6, it is illustrated that the user 10 may be the operator of an aircraft 80. All components similar to the previous embodiment of the invention are given the same numerical designation. In this case, the transmitter 14 is connected to a plurality of mutually orthogonal radiating loop antennas at 18. The radiating means 18 is fixed with respect to the frame of the aircraft 80. The pilot's helmet 81 is provided with a reticle 26 and a receiving means 28 comprising a plurality of mutually orthogonal loop antennas mounted directly on or within the pilot's helmet 81. The analyzer 16 determines the angular orientation of the pilot's head in the manner previously described such that when the pilot dwells the reticle 26 upon predetermined control positions 85 disposed on the cockpit instrument panel, the pilot thereby designates an avionics system, or the like, to be activated or deactivated by actuation of a manually actuable switch 100. The control positions 85 may for example be the normally manually actuated switches which are used to activate or deactivate the various avionics systems contained within the aircraft. The analyzing means 16 may also be connected to a CRT display 88 for providing the pilot 10 with status information. In this manner, the pilot 10 may activate, deactivate or control any one of a number of avionics systems during periods in his flight regime when both hands and feet are otherwise occupied with the cockpit controls.

The present invention has utility in many environments and may, for example, be used as a work station selector in a process control system. The operator of the process, or equipment, may designate work stations by pointing at a schematic-like control board or pointing directly at the equipment to be actuated.

The inventive concept also encompasses a method for electromagnetically communicating and/or switching apparatus comprising the steps of providing a plurality of radiating means having independent components defining a reference coordinate frame, applying to the radiating means electrical signals which generate a plurality of radio frequency electromagnetic fields the signals being multiplexed so that the electromagnetic fields are distinguishable from one another. An array of control positions are provided the control positions being defined with respect to the reference coordinate frame. A plurality of receiving means are provided having independent components for detecting and measuring the electromagnetic fields generated by each of the radiating means. Sighting means is provided for defining the line-of-sight of the operator and the receiving means and sighting means are both mounted on the head of the operator. The operator then points the sighting means to selective control positions within the array of control positions and the output of the receiving means is analyzed and converted into receiver position and orientation with respect to the radiating means. This analyzing step thus determines the control positions to which the operator points the means for sighting. When the operator dwells the means for sighting on one of the control positions for a predetermined time period, a control means associated with the predetermined control position is switched.

The above description should be considered as exemplary and that of the preferred embodiment only. The true spirit and scope of the present invention should be determined by reference to the appended claims. It is desired to include within the appended claims all modifications of the invention that come within the proper scope of the invention.

The embodiments of the invention in which an exclusive property or privlege is claimed are defined as follows:

1. An electromagnetic communications and switching system for use as an invalid communications device comprising:
a plurality of radiating means having independent components defining a reference coordinate frame;
transmitter means for applying to said plurality of radiating means electrical signals which generate a plurality of radio frequency electromagnetic fields, said plurality of electromagnetic fields being distinguishable from one another;
an array of control positions for simulating an alphanumeric keyboard;
a plurality of receiving means, said receiving means having a plurality of independent components for detecting and measuring each of said electromagnetic fields;
means for mounting said receiving means on the head of an operator;
sighting means for defining a line-of-sight for an operator, said sighting means being disposed on said means for mounting in a known relationship with respect to said receiving means, said sighting means thereby being directable by the operator to selectively point to control positions in said array of control positions; and
analyzing means associated with said receiving means for converting the components of said electromagnetic fields received by said receiving means into the position and orientation of said receiving means with respect to said radiating means and thus determining the control positions to which an operator points said sighting means, said analyzing means including means for compiling and displaying a message written by an operator, the operator assembling a message by sequentially pointing said sighting means to control positions on said keyboard.

2. An electromagnetic communications and switching system for remote selection and actuation of an apparatus comprising:
a plurality of radiating means having independent components defining a reference coordinate frame;
transmitter means for applying to said plurality of radiating means electrical signals which generate a plurality of radio frequency electromagnetic fields, said plurality of electromagnetic fields being distinguishable from one another;
an array of control positions associated with the operation of a designated apparatus;
a plurality of receiving means, said receiving means having a plurality of independent components for detecting and measuring each of said electromagnetic fields;
means for mounting said receiving means on the head of an operator;
sighting means for defining a line-of-sight for an operator, said sighting means being disposed on said means for mounting in a known relationship with respect to said receiving means, said sighting means thereby being directable by the operator to selectively point to control positions in said array of control positions; and analyzing means associated with said receiving means for converting the components of said electromagnetic fields received by said receiving means into the position and orientation of said receiving means with respect to said radiating means and thus determining the control positions to which an operator points sighting means, said analyzing means including means for selectively designating a predetermined apparatus when the operator dwells said sighting means on a predetermined portion of said array of control positions and means for actuating the apparatus so designated.

3. A method for electromagnetically communicating and for switching apparatus comprising the steps of:

providing a plurality of radiating means having independent components defining a reference coordinate frame;

applying to said plurality of radiating means electrical signals which generate a plurality of radio frequency electromagnetic fields, said plurality of electromagnetic fields being distinguishable from one another;

providing a plurality of receiving means having independent components for detecting said electromagnetic fields transmitted by said radiating means;

providing an array of control positions;

providing sighting means for defining the line-of-sight for an operator;

mounting said receiving means and said sighting means on the head of an operator;

pointing said sighting means to selective control positions within said array of control positions;

analyzing the output of said receiving means and converting the components of said electromagnetic fields received by said receiving means into the position and orientation of the receiving means with respect to said radiating means and thus determining the control positions to which an operator points said sighting means; and switching a control means associated with each of said control positions when the operator dwells said sighting means on one of said control positions for a predetermined time period.

* * * * *